US009388114B2

(12) United States Patent
Weakley et al.

(10) Patent No.: US 9,388,114 B2
(45) Date of Patent: Jul. 12, 2016

(54) COMPOSITIONS INCLUDING AN ALKYL 3-HYDROXYBUTYRATE

(71) Applicant: Eastman Chemical Company, Kingsport, TN (US)

(72) Inventors: Garry Kenneth Weakley, Kingsport, TN (US); Charles Everette Kelly, Kingsport, TN (US); Therese T. Golob, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 289 days.

(21) Appl. No.: 13/957,657

(22) Filed: Aug. 2, 2013

(65) Prior Publication Data

US 2015/0034866 A1 Feb. 5, 2015

(51) Int. Cl.
| | |
|---|---|
| C07C 31/10 | (2006.01) |
| C07C 53/128 | (2006.01) |
| C07C 59/01 | (2006.01) |
| C07C 31/12 | (2006.01) |
| C07C 31/125 | (2006.01) |
| C09D 7/00 | (2006.01) |
| C11D 3/20 | (2006.01) |
| C11D 7/26 | (2006.01) |
| C11D 7/50 | (2006.01) |
| C23G 5/032 | (2006.01) |
| C23G 5/06 | (2006.01) |

(52) U.S. Cl.
CPC ............... *C07C 59/01* (2013.01); *C07C 31/10* (2013.01); *C07C 31/12* (2013.01); *C07C 31/125* (2013.01); *C07C 53/128* (2013.01); *C09D 7/001* (2013.01); *C09D 7/005* (2013.01); *C11D 3/2093* (2013.01); *C11D 7/266* (2013.01); *C11D 7/5022* (2013.01); *C23G 5/032* (2013.01); *C23G 5/06* (2013.01)

(58) Field of Classification Search
None
See application file for complete search history.

(56) References Cited

U.S. PATENT DOCUMENTS

| | | | |
|---|---|---|---|
| 2,351,366 A | 6/1944 | Pohl et al. | |
| 2,396,278 A | 3/1946 | Lind | |
| 2,486,921 A | 11/1949 | Byerly | |
| 2,486,922 A | 11/1949 | Strain | |
| 2,847,423 A | 8/1958 | Lacey | |
| 3,332,880 A | 7/1967 | Kessler et al. | |
| 3,513,189 A | 5/1970 | Marcus | |
| 4,005,189 A | 1/1977 | Reese et al. | |
| 4,994,602 A | 2/1991 | Seido et al. | |
| 5,183,929 A | 2/1993 | Naito et al. | |
| 5,420,335 A | 5/1995 | Birkhahn et al. | |
| 5,508,435 A | 4/1996 | Armstrong, III et al. | |
| 5,519,161 A | 5/1996 | Birkhahn et al. | |
| 5,612,303 A | 3/1997 | Takayanagi et al. |
| 5,686,489 A | 11/1997 | Yu et al. |
| 5,693,850 A | 12/1997 | Birkhahn et al. |
| 5,800,897 A | 9/1998 | Sharma et al. |
| 5,876,621 A | 3/1999 | Sapienza |
| 5,980,774 A | 11/1999 | Sapienza |
| 6,043,063 A | 3/2000 | Kurdikar et al. |
| 6,075,154 A | 6/2000 | Gonda et al. |
| 6,083,729 A | 7/2000 | Martin et al. |
| 6,307,094 B1 | 10/2001 | Chong et al. |
| 6,492,545 B2 | 12/2002 | Saito et al. |
| 6,586,152 B1 | 7/2003 | Urano et al. |
| 6,709,848 B1 | 3/2004 | Martin et al. |
| 6,818,789 B2 | 11/2004 | Fleming et al. |
| 6,843,931 B2 | 1/2005 | Sapienza |
| 6,844,447 B2 | 1/2005 | Zhong et al. |
| 6,897,338 B2 | 5/2005 | Zhong et al. |
| 6,933,404 B2 | 8/2005 | Zhong et al. |
| 6,939,981 B1 | 9/2005 | Boaz |
| 7,001,969 B2 | 2/2006 | Zhong et al. |
| 7,057,064 B2 | 6/2006 | Proctor et al. |
| 7,166,743 B2 | 1/2007 | Zhong et al. |
| 7,230,144 B2 | 6/2007 | Zhong et al. |
| 7,419,759 B2 | 9/2008 | Kim et al. |
| 7,485,452 B2 | 2/2009 | Hwang et al. |
| 7,563,385 B2 | 7/2009 | Sapienza |
| 7,795,376 B2 | 9/2010 | Van Walsem et al. |
| 8,338,145 B2 | 12/2012 | Tsobanakis et al. |
| 8,642,654 B2 | 2/2014 | Clarke et al. |
| 2005/0221457 A1 | 10/2005 | Tsobanakis et al. |
| 2006/0078596 A1 | 4/2006 | Clarke et al. |

(Continued)

FOREIGN PATENT DOCUMENTS

| | | |
|---|---|---|
| EP | 1502584 A1 | 2/2005 |
| EP | 1537247 B1 | 9/2007 |

(Continued)

OTHER PUBLICATIONS

Notification of Transmittal of the International Search Report and the Written Opinion of the International Searching Authority with Date of Mailing Oct. 15, 2014 for International Application No. PCT/US2014/047528.
Wanfang Li, et al.; "Ru-Catalyzed Asymmetric Hydrogenation of 3-Oxoglutaric Acid Derivatives via Solvent-Assisted Pinpoint Recognition of Carbonyls in Close Chemical Propinquity"; Organic Letters, 2011, vol. 13, No. 15, 3876-3879.
Sven-Olov Lawesson et al.; "t-Butyl Acetoacetate"; Organic Syntheses, Coll. vol. 5, p. 155 (1973); vol. 42, p. 28 (1962).
USPTO Office Action dated Nov. 7, 2014 for co-pending U.S. Appl. No. 13/957,616.

(Continued)

*Primary Examiner* — Tanisha Diggs
(74) *Attorney, Agent, or Firm* — Hovey Williams LLP

(57) ABSTRACT

Compositions comprising an alkyl 3-hydroxybutyrate and one or more additional components are provided. The compositions of the present invention may include at least one alkyl 3-hydroxybutyrate having at least 3 and not more than 5 carbon atoms, along with one or more additional components including, for example, alkyl butyrates, alkyl acetates, alkyl alcohols, and dimers and/or trimers of the alkyl 3-hydroxybutyrate. Such compositions may be products of, for example, the hydrogenation of an acetoacetate-containing composition.

9 Claims, No Drawings

(56) References Cited

U.S. PATENT DOCUMENTS

| | | |
|---|---|---|
| 2006/0251597 A1 | 11/2006 | Van Scott et al. |
| 2007/0082832 A1 | 4/2007 | DiCosimo et al. |
| 2007/0117252 A1* | 5/2007 | Ogihara .................. C08G 77/48 438/72 |
| 2007/0208183 A1 | 9/2007 | Haan et al. |
| 2008/0038802 A1 | 2/2008 | Hwang et al. |
| 2008/0287538 A1 | 11/2008 | Scholz et al. |
| 2009/0122410 A1* | 5/2009 | Tamura .................. C08L 83/10 359/601 |
| 2009/0298144 A1 | 12/2009 | Tsobanakis et al. |
| 2010/0055628 A1* | 3/2010 | McMurry .................. C10L 1/02 431/11 |
| 2010/0119939 A1 | 5/2010 | Misumi et al. |
| 2010/0286017 A1 | 11/2010 | Righetto |
| 2011/0101268 A1 | 5/2011 | Choi et al. |
| 2011/0107660 A1 | 5/2011 | Chen et al. |
| 2011/0143149 A1* | 6/2011 | Shibayama .......... C09D 183/08 428/447 |
| 2011/0151379 A1 | 6/2011 | Choi et al. |
| 2011/0195839 A1 | 8/2011 | Schlotterbeck et al. |
| 2011/0195846 A1 | 8/2011 | Troppmann et al. |
| 2012/0064611 A1 | 3/2012 | Robertson et al. |
| 2012/0317736 A1 | 12/2012 | Gonzales et al. |
| 2013/0102663 A1 | 4/2013 | Clarke |
| 2014/0194509 A1 | 7/2014 | Clarke et al. |
| 2014/0308719 A1 | 10/2014 | Clarke et al. |
| 2015/0065571 A1 | 3/2015 | Clarke et al. |

FOREIGN PATENT DOCUMENTS

| | | |
|---|---|---|
| EP | 1601737 B1 | 10/2007 |
| FR | 2 577 922 A1 | 8/1986 |
| GB | 2511941 A | 9/2014 |
| JP | 2009-173880 A | 8/2009 |
| KR | 2006024550 A | 3/2006 |
| WO | 2011/039661 A2 | 4/2011 |
| WO | 2012/039516 A1 | 3/2012 |
| WO | 2014/139599 A1 | 9/2014 |

OTHER PUBLICATIONS

Notification of Transmittal of the International Search Report and the Written Opinion of the International Searching Authority with Date of Mailing Dec. 3, 2014 for International Application No. PCT/US2014/047531.

Notification of Transmittal of the International Search Report and the Written Opinion of the International Searching Authority with Date of Mailing Dec. 3, 2014 for International Application No. PCT/US2014/047524.

Notification of Transmittal of the International Search Report and the Written Opinion of the International Searching Authority with Date of Mailing Dec. 3, 2014 for International Application No. PCT/US2014/047526.

USPTO Office Action dated Jan. 5, 2015 for co-pending U.S. Appl. No. 13/957,642.

Notice of Allowance for related U.S. Appl. No. 13/957,616, filed Aug. 2, 2013, dated Mar. 11, 2015, 7 pages.

E.I. Klabunovskii, et al.; Reaction Kinetics and Catalysis Letters, vol. 2, No. 3, 291-296 (1975) on the Asymmetrizing and Catalytic Activity of Ru Catalysts.

USPTO Office Action dated Apr. 16, 2014 for co-pending U.S. Appl. No. 13/957,642.

Lusty, C.J. et al., Poly-β-Hydroxybutyrate Depolymerases of Pseudomonas Lemoignei*, Department of Bacteriology and Immunology, University of California, Berkeley, vol. 56, Jul. 12, 1966, pp. 960-965.

Notice of Allowance dated May 11, 2015 for co-pending U.S. Appl. No. 13/957,616, 8 pages.

Notice of Allowance dated Jun. 8, 2015 for co-pending U.S. Appl. No. 13/957,616, 7 pages.

Office Action dated Feb. 12, 2015 for co-pending U.S. Appl. No. 13/957,631, 10 pages.

Office Action dated Jun. 4, 2015 for co-pending U.S. Appl. No. 13/957,642, 12 pages.

Laird, Chemical Industry Digest, How to Minimize Scale Up Difficulties, Jul. 2010, pp. 51-56.

Wrightson et al., Safety Issues in the Scale-Up of Chemical Reactions, 2013, pp. 1-6, www.rsc.org.

Notice of Allowance dated Jun. 26, 2015 for related U.S. Patent Application No. 13/957,616, filed Aug. 2, 2013, 8 pages.

Office Action dated Jul. 13, 2015 for related U.S. Appl. No. 14/694,696; 9 pages.

Office Action dated Mar. 2, 2016 for related U.S. Appl. No. 14/685,314, filed Apr. 13, 2015, 32 pages.

Final Office Action dated Aug. 25, 2015 in related U.S. Appl. No. 13/957,631, filed Aug. 2, 2013, 12 pages.

Advisory Action dated Sep. 1, 2015 in related U.S. Appl. No. 13/957,631, filed Aug. 2, 2013, 4 pages.

ASTM D1160, Mar. 2013.

ASTM D7236-07, Jan. 2008.

ASTM E659-78, Dec. 2005.

ASTM D4052-11, Dec. 2011.

ASTM D4488, Jun. 1995.

Vuitel et al., "Etude de la reactivite de la function carbonyle avec le cetene en presence d'un alcoyde de titane", Helvetica Chemica Acta, vol. 57, pp. 1713-1718 (1974).

Riis et al., "Gas chromatograph determination of poly-β-hydroxybutyric acid in microbial biomass after hydrochloric acid propanolysis",Journal of Chromatography, vol. 445, pp. 285-289 (1988).

Adkins, et al., "The Hydrogenation of Acetoacetic Ester and Certain of its Derivatives Over Nickel", J. Am. Chem. Soc., vol. 52, pp. 5192-5198 (1930).

Co-pending U.S. Appl. No. 13/957,642, filed Aug. 2, 2013.
Co-pending U.S. Appl. No. 13/957,616, filed Aug. 2, 2013.
Co-pending U.S. Appl. No. 13/957,631, filed Aug. 2, 2013.

* cited by examiner

COMPOSITIONS INCLUDING AN ALKYL 3-HYDROXYBUTYRATE

FIELD OF THE INVENTION

This invention relates to compositions including an alkyl ester. More specifically, this invention relates to compositions comprising an alkyl hydroxybutyrate.

BACKGROUND

Alkyl esters, and in particular, alkyl hydroxybutyrates may be useful in a variety of different end-use applications. For example, alkyl hydroxybutyrates may be employed as pharmaceutical intermediates or as fragrances or other additives in a variety of consumer products. Recently, it has been discovered that alkyl hydroxybutyrates may be useful as organic cleaning solvents and, when used in combination with water and an optional surfactant, provide cleaning compositions that are highly effective, while being both environmentally benign and non-toxic. Current methods of obtaining alkyl hydroxybutyrates include extraction of a polyhydroxybutyrate (PHB) from plant materials or other biomass, which is expensive, time consuming, and difficult to control. Additionally, this type of synthesis is nearly impossible to carry out on a large scale.

Thus, a need exists for an efficient method of producing an alkyl hydroxybutyrate, which can consistently provide a high-purity product in a time- and cost-effective manner.

SUMMARY

In one aspect, the present invention concerns a composition comprising:
  (a) at least one alkyl 3-hydroxybutyrate defined by formula (I):

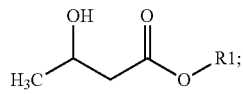

(b) one or more additional component selected from the group consisting of—
    (i) an alkyl butyrate defined by formula (II):

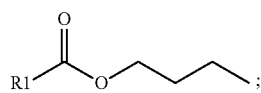

(ii) a dimer and/or trimer of the alkyl 3-hydroxybutyrate; and
    (iii) an alkyl acetate defined by formula (III):

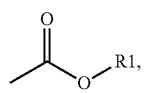

wherein R1 is an alkyl group having at least three carbon atoms and is the same in each of formulas (I), (II), and (III).

In another aspect, the present invention concerns a composition comprising:
  (a) at least one alkyl 3-hydroxybutyrate defined by formula (I):

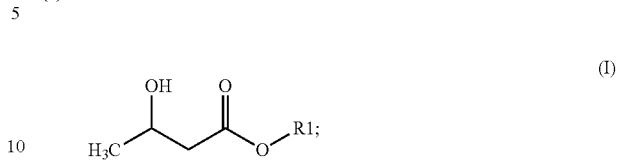

and
  (b) at least one alkyl butyrate defined by formula (II):

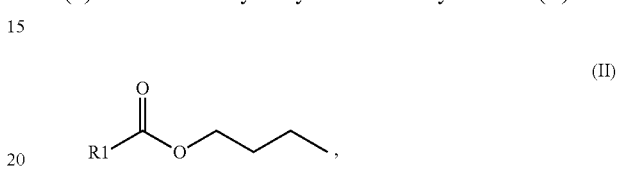

wherein R1 has least three and not more than five carbon atoms, wherein R1 in formula (I) and R1 in formula (II) are the same.

DETAILED DESCRIPTION

In some aspects, the present invention relates to compositions including an alkyl 3-hydroxybutyrate. The alkyl 3-hydroxybutyrate included in compositions of the present invention may be represented by the following formula:

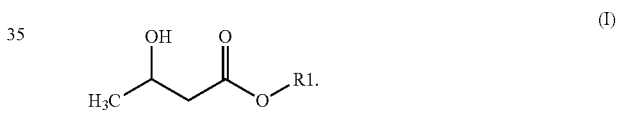

The group R1 in formula (I) above may be an alkyl group and can have at least 3 and not more than 5 carbon atoms. As used herein, the term "alkyl group," refers to a branched or straight-chain monovalent alkyl radical. The R1 group can be an alkyl group that includes 3 or 4 carbon atoms, or may include 4 carbon atoms. The R1 group can be an alkyl group selected from the group consisting of isopropyl, n-propyl, isobutyl, n-butyl, 2-butyl (sec-butyl), 2,2-dimethylethyl (tert-butyl), 3,3-dimethylpentyl (isopentyl), 1-pentyl (n-pentyl), 1-methylbutyl (2-pentyl), 2-methylbutyl, 2-ethylpropyl (3-pentyl), 1,1-dimethylpropyl, 1,2-dimethylpropyl, 2,2-dimethylpropyl (neopentyl), and cyclopentyl, or may be selected from the group consisting of isopropyl, n-propyl, isobutyl, n-butyl, and 2-butyl. In some cases, the R1 group may be an alkyl group selected from the group consisting of isopropyl, isobutyl, n-butyl, and 2-butyl or the group consisting of isobutyl, n-butyl, and 2-butyl. Also, the R1 group can be n-butyl. The alkyl 3-hydroxybutyrate may be non-halogenated.

The alkyl 3-hydroxybutyrate can be present in the composition in an amount of at least about 40 weight percent, at least about 50 weight percent, at least about 65 weight percent, at least about 75 weight percent, at least about 80 weight percent, at least about 90 weight percent and/or not more than about 99.9 weight percent, not more than about 99 weight percent, not more than about 95 weight percent, based on the total weight of the composition. The alkyl 3-hydroxybutyrate can be present in the composition in an amount in the range of from about 40 to about 99.9 weight percent, about 40 to about 99 weight percent, about 40 to about 95 weight percent, about 50 to about 99.9 weight percent, about 50 to about 99 weight percent, about 50 to about 95 weight percent, about 65 to about 99.9 weight percent, about 65 to about 99 weight percent, about 65 to about 95 weight percent, about 75 to about 99.9 weight percent, about 75 to about 99 weight percent, about 75 to about 95 weight percent, about 80 to about 99.9 weight percent, about 80 to about 99 weight percent, about 80 to about 95 weight percent, about 90 to about 99.9 weight percent, about 90 to about 99 weight percent, about 90 to about 95 weight percent, based on the total weight of the composition.

In addition to the alkyl 3-hydroxybutyrate defined by formula (I) above, the composition of the present invention may also comprise at least alkyl butyrate defined by the following formula:

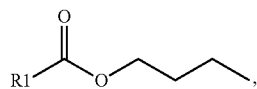
(II)

wherein the R1 group of formula (II) may be an alkyl group having at least 3 and not more than 5 carbon atoms. The R1 group of formula (I) and the R1 group of formula (II) may be the same. The R1 group in formula (III) can include 3 or 4 carbon atoms or it may include 4 carbon atoms. The R1 group may be selected from the group consisting of isopropyl, n-propyl, isobutyl, n-butyl, 2-butyl (sec-butyl), isopentyl, pentyl, and 2,2-dimethylpropyl, or may be selected from the group consisting of isopropyl, n-propyl, isobutyl, n-butyl, and 2-butyl. In some cases, the R1 group may be selected from the group consisting of isopropyl, isobutyl, n-butyl, and 2-butyl or the group consisting of isobutyl, n-butyl, and 2-butyl. The R1 group can be n-butyl.

The alkyl butyrate described by formula (II) above can be present in the composition in an amount of at least about 50 parts per million by weight (ppmw), at least about 100 ppmw, at least about 150 ppmw, at least about 200 ppmw and/or not more than about 0.5 weight percent, not more than about 0.1 weight percent, not more than about 1500 ppmw, not more than about 1000 ppmw, not more than 750 ppmw, or not more than 500 ppmw, or in an amount in the range of from about 50 ppmw to about 0.5 weight percent, about 50 ppmw to about 0.1 weight percent, about 50 ppmw to about 1500 ppmw, about 50 ppmw to about 1000 ppmw, about 50 ppmw to about 750 ppmw, about 50 ppmw to about 500 ppmw, about 100 ppmw to about 0.5 weight percent, about 100 ppmw to about 0.1 weight percent, about 100 ppmw to about 1500 ppmw, about 100 ppmw to about 1000 ppmw, about 100 ppmw to about 750 ppmw, about 100 ppmw to about 500 ppmw, about 150 ppmw to about 0.5 weight percent, about 150 ppmw to about 0.1 weight percent, about 150 ppmw to about 1500 ppmw, about 150 ppmw to about 1000 ppmw, about 150 ppmw to about 750 ppmw, about 150 ppmw to about 500 ppmw, about 200 ppmw to about 0.5 weight percent, about 200 ppmw to about 0.1 weight percent, about 200 ppmw to about 1500 ppmw, about 200 ppmw to about 1000 ppmw, about 200 ppmw to about 750 ppmw, about 200 ppmw to about 500 ppmw, based on the total weight of the composition.

In some cases, the composition of the present invention can include not more than about 10 weight percent, not more than about 5 weight percent, not more than about 2 weight percent, not more than about 1 weight percent, not more than about 0.5 weight percent, not more than about 1000 ppmw of one or more components other than the alkyl 3-hydroxybutyrate and the alkyl butyrate.

The composition may, however, comprise at least one additional component selected from the group consisting of an alkyl acetate, one or more alkyl alcohols, a second alkyl 3-hydroxybutyrate, an alkyl 3-hydroxy-2-methylbutyrate, and a dimer and/or trimer of at least one of the alkyl 3-hydroxybutyrates. The alkyl groups of the additional components may be the same as the alkyl group R1 in the alkyl 3-hydroxybutyrate and alkyl butyrate defined by formulas (I) and (II), above, or at least one of the additional components may comprise an alkyl group different from the alkyl group of the alkyl 3-hydroxybutyrate and alkyl butyrate shown above. In some cases, two or more of the additional additives listed above may be present in the composition. For example, the composition may include an alkyl acetate and an alkyl butyrate or the composition may include an alkyl acetate, an alkyl butyrate, and a dimer and/or trimer of at least one alkyl 3-hydroxybutyrate. The composition may also include each of the additional components listed above in an amount as described below.

The composition of the present invention can include not more than about 10 weight percent, not more than about 5 weight percent, not more than about 2 weight percent, not more than about 1 weight percent, not more than about 0.5 weight percent, not more than about 1000 ppmw of one or more components other than the alkyl 3-hydroxybutyrate and one or more additional components. Additionally, or in the alternative, the composition of the present invention can include not more than about 5 weight percent, not more than about 2 weight percent, not more than about 1 weight percent, not more than about 0.5 weight percent, not more than about 1000 ppmw of one or more components other than the alkyl 3-hydroxybutyrate, the alkyl butyrate, and one or more additional components.

The one or more additional components may be present in the composition in a total amount of at least about 50 parts per million by weight (ppmw), at least about 100 ppmw, at least about 150 ppmw, at least about 200 ppmw and/or not more than about 0.5 weight percent, not more than about 0.1 weight percent, not more than about 1500 ppmw, not more than about 1000 ppmw, not more than 750 ppmw, or not more than 500 ppmw, or in an amount in the range of from about 50 ppmw to about 0.5 weight percent, about 50 ppmw to about 0.1 weight percent, about 50 ppmw to about 1500 ppmw, about 50 ppmw to about 1000 ppmw, about 50 ppmw to about 750 ppmw, about 50 ppmw to about 500 ppmw, about 100 ppmw to about 0.5 weight percent, about 100 ppmw to about 0.1 weight percent, about 100 ppmw to about 1500 ppmw, about 100 ppmw to about 1000 ppmw, about 100 ppmw to about 750 ppmw, about 100 ppmw to about 500 ppmw, about 150 ppmw to about 0.5 weight percent, about 150 ppmw to about 0.1 weight percent, about 150 ppmw to about 1500 ppmw, about 150 ppmw to about 1000 ppmw, about 150 ppmw to about 750 ppmw, about 150 ppmw to about 500 ppmw, about 200 ppmw to about 0.5 weight percent, about 200 ppmw to about 0.1 weight percent, about 200 ppmw to about 1500 ppmw, about 200 ppmw to about 1000 ppmw, about 200 ppmw to about 750 ppmw, about 200 ppmw to about 500 ppmw, based on the total weight of the composition.

When the composition of the present invention comprises an alkyl acetate, the alkyl acetate may be defined by formula (III):

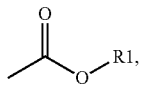
(III)

wherein the R1 group of formula (III) may be an alkyl group having at least 3 and not more than 5 carbon atoms. The R1 group of formulas (I), (II), and (III) may be the same. The R1 group in formula (III) can include 3 or 4 carbon atoms or it may include 4 carbon atoms. The R1 group may be selected from the group consisting of isopropyl, n-propyl, isobutyl, n-butyl, 2-butyl (sec-butyl), isopentyl, pentyl, and 2,2-dimethylpropyl, or may be selected from the group consisting of isopropyl, n-propyl, isobutyl, n-butyl, and 2-butyl. In some cases, the R1 group may be selected from the group consisting of isopropyl, isobutyl, n-butyl, and 2-butyl or the group consisting of isobutyl, n-butyl, and 2-butyl. The R1 group can be n-butyl.

The alkyl acetate may be present in the composition in an amount of at least about 50 ppmw, at least about 100 ppmw, at least about 150 ppmw, at least about 200 ppmw and/or not more than about 1000 ppmw, not more than about 800 ppmw, not more than about 500 ppmw, or in an amount in the range of from about 50 to about 1000 ppmw, about 50 to about 800 ppmw, about 50 to about 500 ppmw, about 100 to about 1000 ppmw, about 100 to about 800 ppmw, about 100 to about 500 ppmw, about 150 to about 1000 ppmw, about 150 to about 800 ppmw, about 150 to about 500 ppmw, about 200 to about 1000 ppmw, about 200 to about 800 ppmw, about 200 to about 500 ppmw, based on the total weight of the composition.

When the composition includes at least one alkyl alcohol, the alcohol may be defined by formula (IV):

R1-OH (IV), wherein the R1 group of formula (IV) may be an alkyl group having at least 3 and not more than 5 carbon atoms. The R1 group of formulas (I), (II), (III), and (IV) may be the same. The R1 group in formula (IV) can include 3 or 4 carbon atoms or it may include 4 carbon atoms. The R1 group may be selected from the group consisting of isopropyl, n-propyl, isobutyl, n-butyl, 2-butyl (sec-butyl), isopentyl, pentyl, and 2,2-dimethylpropyl, or may be selected from the group consisting of isopropyl, n-propyl, isobutyl, n-butyl, and 2-butyl. In some cases, the R1 group may be selected from the group consisting of isopropyl, isobutyl, n-butyl, and 2-butyl or the group consisting of isobutyl, n-butyl, and 2-butyl. The R1 group can be n-butyl.

The alcohol defined by formula (IV) above may be present in the inventive composition in an amount of at least about 3500 ppmw, at least about 4500 ppmw, at least about 5000 ppmw and/or not more than 10,000 ppmw, not more than 9500 ppmw, not more than 8500 ppmw or an amount in the range of from about 3500 to about 10,000 ppmw, about 3500 to about 9500 ppmw, about 3500 to about 8500 ppmw, about 4500 to about 10,000 ppmw, about 4500 to about 9500 ppmw, about 4500 to about 8500 ppmw, about 5000 to about 10,000 ppmw, about 5000 to about 9500 ppmw, about 5000 to about 8500 ppmw, based on the total weight of the composition.

The composition of the present invention may further include a second alkyl alcohol defined by formula (V):

R2-OH (V), wherein the R2 group of formula (V) may be an alkyl group having at least 2 and not more than 4 carbon atoms. The R2 group may include one less carbon than the R1 group of formulas (I), (II), (III), and (IV). The R2 group in formula (V) can include 2 or 3 carbon atoms or it may include 3 carbon atoms. The R2 group may be selected from the group consisting of ethyl, isopropyl, n-propyl, isobutyl, n-butyl, 2-butyl (sec-butyl), or may be selected from the group consisting of ethyl, isopropyl, n-propyl. In some cases, the R2 group may be a propyl group selected from isopropyl and n-propyl.

The second alkyl alcohol may be present in the composition in an amount of at least about 50 ppmw, at least about 100 ppmw, at least about 150 ppmw, at least about 200 ppmw and/or not more than about 1200 ppmw, not more than about 1000 ppmw, not more than about 800 ppmw, or in an amount in the range of from about 50 to about 1200 ppmw, about 50 to about 1000 ppmw, about 50 to about 800 ppmw, about 100 to about 1200 ppmw, about 100 to about 1000 ppmw, about 100 to about 800 ppmw, about 150 to about 1200 ppmw, about 150 to about 1000 ppmw, about 150 to about 800 ppmw, about 200 to about 1000 ppmw, about 200 to about 800 ppmw, about 200 to about 500 ppmw, based on the total weight of the composition.

Additionally, the composition may include at least one other alkyl 3-hydroxybutyrate defined by formula (VI):

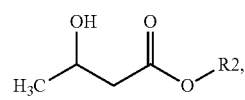
(VI)

wherein the R2 group of formula (VI) may be an alkyl group having at least 2 and not more than 5 carbon atoms. The R2 group may include one less carbon than the R1 group of formulas (I), (II), (III), and (IV) and/or may be the same as the R2 group of formula (V). The R2 group in formula (VI) can include 2, 3, or 4 carbon atoms. The R2 group may be selected from the group consisting of ethyl, isopropyl, n-propyl, isobutyl, n-butyl, 2-butyl (sec-butyl), or t-butyl, or it may be selected from the group consisting of ethyl, isopropyl, n-propyl, and t-butyl. In some cases, the R2 group may be a propyl group selected from isopropyl and n-propyl or it may be t-butyl. The composition may include two other alkyl 3-hydroxybutyrate other than the alkyl 3-hydroxybutyrate defined by formula (I), and, in some cases, the additional 3-hydroxybutyrates may have different R2 groups.

The additional 3-hydroxybutyrate or 3-hydroxybutyrates may be present in the composition in an amount of at least about 50 ppmw, at least about 100 ppmw, at least about 150 ppmw, at least about 200 ppmw and/or not more than about 1000 ppmw, not more than about 800 ppmw, not more than about 500 ppmw, not more than about 200 ppmw, or in an amount in the range of from about 50 to about 1000 ppmw, about 50 to about 800 ppmw, about 50 to about 500 ppmw, about 50 to about 200 ppmw, about 100 to about 1000 ppmw, about 100 to about 800 ppmw, about 100 to about 500 ppmw, about 100 to 200 ppmw, about 150 to about 1000 ppmw, about 150 to about 800 ppmw, about 150 to about 500 ppmw, 150 to about 200 ppmw, about 200 to about 1000 ppmw, about 200 to about 800 ppmw, about 200 to about 500 ppmw, based on the total weight of the composition.

The composition may also include at least one alkyl 3-hydroxy-2-methyl butyrate defined by formula (VII):

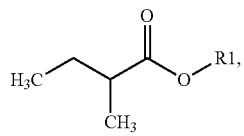

(VII)

wherein the R1 group of formula (VII) may be an alkyl group having at least 3 and not more than 5 carbon atoms. The R1 group of formula (VII) may be the same as the R1 group in formulas (I), (II), (III), and (IV). The R1 group in formula (VII) can include 3 or 4 carbon atoms or it may include 4 carbon atoms. The R1 group may be selected from the group consisting of isopropyl, n-propyl, isobutyl, n-butyl, 2-butyl (sec-butyl), isopentyl, pentyl, and 2,2-dimethylpropyl, or may be selected from the group consisting of isopropyl, n-propyl, isobutyl, n-butyl, and 2-butyl. In some cases, the R1 group may be selected from the group consisting of isopropyl, isobutyl, n-butyl, and 2-butyl or the group consisting of isobutyl, n-butyl, and 2-butyl. The R1 group can be n-butyl.

The alkyl 3-hydroxy-2-methylbutyrate may be present in the composition in an amount of at least about 50 ppmw, at least about 100 ppmw, at least about 200 ppmw, at least about 300 ppmw and/or not more than about 1200 ppmw, not more than about 1000 ppmw, not more than about 800 ppmw, based on the total weight of the composition. The alkyl 3-hydroxy-2-methylbutyrate may be present in an amount in the range of from about 50 to about 1200 ppmw, about 50 to about 1000 ppmw, about 50 to about 800 ppmw, about 100 to about 1200 ppmw, about 100 to about 1000 ppmw, about 100 to about 800 ppmw, about 200 to about 1200 ppmw, about 200 to about 1000 ppmw, about 200 to about 800 ppmw, about 300 to about 1200 ppmw, about 300 to about 1000 ppmw, about 300 to about 800 ppmw, based on the total weight of the composition.

The composition of the present invention may also include a dimer and/or trimer of the alkyl 3-hydroxybutyrate defined by formula (I) above. Depending on the alkyl group, the dimer may be a 4-alkoxy-4-oxobutan-2-yl 3-hydroxybutyrate, with the alkoxy group selected from the group consisting of a propoxy or butoxy group. The dimer and/or trimer may be present in the composition in an amount of at least about 50 ppmw, at least about 100 ppmw, at least about 200 ppmw and/or not more than about 1200 ppmw, not more than about 1000 ppmw, not more than about 800 ppmw, based on the total weight of the composition. The alkyl 3-hydroxy-2-methylbutyrate may be present in an amount in the range of from about 50 to about 1200 ppmw, about 50 to about 1000 ppmw, about 50 to about 800 ppmw, about 100 to about 1200 ppmw, about 100 to about 1000 ppmw, about 100 to about 800 ppmw, about 200 to about 1200 ppmw, about 200 to about 1000 ppmw, about 200 to about 800 ppmw, based on the total weight of the composition.

It may be preferable that the composition described herein is not formed by blending two or more of the components listed above. Instead, at least one of the components of the inventive composition may be generated in situ, as the result of, for example, one or more chemical reactions. The composition of the present invention may be a reaction composition such as, for example, a composition produced during the synthesis of an alkyl 3-hydroxybutyrate.

The composition of the present invention may result from hydrogenation of a precursor reaction composition comprising an alkyl acetoacetate. During hydrogenation, at least a portion of the precursor composition may have been contacted with a hydrogen-containing gas, optionally in the presence of a catalyst, to convert at least a portion of the alkyl acetoacetate to an alkyl 3-hydroxybutyrate as defined by formula (I). Additionally, one or more of the other components defined by formulas (II) through (VII) may also be formed as the result of the hydrogenation of various other components and impurities present in the precursor reaction mixture.

The hydrogenation conditions to which the precursor reaction composition may be exposed includes a temperature of at least about 60° C., at least about 65° C., at least about 70° C. and/or not more than about 100° C., not more than about 95° C., not more than about 90° C. or in the range of from about 60 to about 100° C., about 60 to about 95° C., about 60 to about 90° C., about 65 to about 100° C., about 65 to about 95° C., about 65 to about 90° C., about 70 to about 100° C., about 70 to about 95° C., about 70 to about 90° C. The hydrogenation conditions may also include a pressure of at least about 300 psig, at least about 500 psig, at least about 800 psig and/or not more than about 2000 psig, not more than about 1500 psig, not more than about 1000 psig or a pressure in the range of from about 300 to about 2000 psig, about 300 to about 1500 psig, about 300 to about 1000 psig, about 500 to about 2000 psig, about 500 to about 1500 psig, about 500 to about 1000 psig, about 800 to about 2000 psig, about 800 to about 1500 psig, about 800 to about 1000 psig. Additionally, during hydrogenation, the pH of the precursor reaction mixture can be neutral and may be at least about 6, at least about 6.5, at least about 7 and/or not more than about 8, not more than about 7.5, not more than about 7.25 or in the range of from about 6 to about 8, about 6 to about 7.5, about 6 to about 7.25, about 6.5 to about 8, about 6.5 to about 7.5, about 6.5 to about 7.25, about 7 to about 8, about 7 to about 7.5, about 7 to about 7.25.

The hydrogenation catalyst used during hydrogenation can be, for example, a heterogeneous catalyst comprising one or more catalytic metals supported in, on, and/or within a catalyst support. The catalytic metal may be selected from the group consisting of palladium, nickel, platinum, and ruthenium and may be present in an amount of at least about 1 weight percent, at least about 2 weight percent, at least about 3 weight percent and/or not more than about 10 weight percent, not more than about 8 weight percent, not more than about 6 weight percent, or in an amount in the range of from about 1 to about 10 weight percent, about 1 to about 8 weight percent, about 1 to about 6 weight percent, about 2 to about 10 weight percent, about 2 to about 8 weight percent, about 2 to about 6 weight percent, about 3 to about 10 weight percent, about 3 to about 8 weight percent, about 3 to about 6 weight percent, based on the total weight of the catalyst. Although catalysts including more than one catalytic metal may be used, the catalyst may alternatively include only a single catalytic metal.

The catalyst support of the hydrogenation catalyst may comprise one or more materials selected from the group consisting of silica, alumina, aluminosilicate, and carbon. Preferably, the catalyst support may be non-acidic and does not include silica or alumina. The catalyst support may comprise or consist essentially of carbon.

The hydrogenation of the precursor solution may be carried out for a period of time of at least about 30 minutes, at least about 1 hour, at least about 2 hours and/or not more than about 8 hours, not more than about 6 hours, not more than about 4 hours or a period of time in the range of from about 30 minutes to about 8 hours, about 30 minutes to about 6 hours, about 30 minutes to about 4 hours, about 1 to about 8 hours, about 1 to about 6 hours, about 1 to about 4 hours, about 2 to about 8 hours, about 2 to about 6 hours, about 2 to about 4 hours in order to obtain an actual yield of alkyl 3-hydroxybutyrate of at least about 50 percent, at least about 60 percent, at least about 70 percent, at least about 80 percent, at least about 85 percent, at least about 90 percent, at least about 95 percent, as compared to theoretical.

The acetoacetate-containing precursor solution may have originated from a variety of suitable sources. For example, the precursor solution may also be the result of another chemical reaction, such as, for example the reaction of diketene with an alkyl alcohol to form alkyl acetoacetate. In this case, the temperature of the diketene-alcohol reaction mixture may be at least about 60° C., at least about 65° C., at least about 70° C. and/or not more than 105° C., not more than about 100° C., not more than about 95° C., or at a target temperature in the range of from about 60 to about 105° C., about 60 to about 100° C., about 60 to about 95° C., about 65 to about 105° C., about 65 to about 100° C., about 65 to about 95° C., about 70 to about 105° C., about 70 to about 100° C., about 70 to about 95° C. and may be maintained at a relatively consistent temperature during the addition of diketene.

The alkyl alcohol, which may be defined by formula (IV) above, may be present in the diketene reaction mixture a stoichiometric excess, based on the amount of diketene introduced the reaction zone. For example, the alcohol may be present in the reaction zone in a stoichiometric excess of at least at least about 1 percent, at least about 2 percent, or at least about 5 percent, based on the total amount of diketene.

At least a portion of the reaction can be carried out in the presence of a catalyst, such as, for example, a homogenous catalyst that is at least partially dissolvable in the reaction medium. The catalyst may be selected from the group consisting of sodium hydroxide, a sodium alkoxide, hydrogen chloride, sulfuric acid, tertiary amines, and combinations thereof or may be a trialkyl amine, such as, for example, triethylamine. The catalyst can be present in an amount of at least about 0.1 weight percent, at least about 1 weight percent, at least about 2 weight percent, at least about 3 weight percent and/or not more than about 10 weight percent, not more than about 8 weight percent, not more than about 6 weight percent, or in an amount in the range of from about 0.1 to about 10 weight percent, about 0.1 to about 8 weight percent, about 0.1 to about 6 weight percent, about 1 to about 10 weight percent, about 1 to about 8 weight percent, about 1 to about 6 weight percent, about 2 to about 10 weight percent, about 2 to about 8 weight percent, about 2 to about 6 weight percent, about 3 to about 10 weight percent, about 3 to about 8 weight percent, about 3 to about 6 weight percent, based on the total weight of the reaction mixture.

Depending on the source of the acetoacetate-containing mixture, the composition of the present invention may also include one or more components resulting from the hydrogenation of residual catalyst or other components remaining in the precursor mixture from previous reactions or processing. For example, when the precursor mixture results from the reaction of diketene and an alkyl alcohol in the presence of an amine catalyst, the inventive composition may include at least one at least partially hydrogenated amine compound. The amount of the at least partially hydrogenated amine compound present in the inventive reaction mixture can depend, at least in part, on the preliminary catalyst loading, as well as the conditions and severity of the hydrogenation step. The amount of amine compound in the inventive composition can be at least about 200 ppmw, at least about 300 ppmw, at least about 500 ppmw and/or not more than about 2000 ppmw, not more than about 1500 ppmw, or not more than about 1000 ppmw, or an amount in the range of from about 200 to about 2000 ppmw, about 200 to about 1500 ppmw, about 200 to about 1000 ppmw, about 300 to about 2000 ppmw, about 300 to about 1500 ppmw, about 300 to about 1000 ppmw, about 500 to about 2000 ppmw, about 500 to about 1500 ppmw, about 500 to about 1000 ppmw, based on the total weight of the composition. One example of an amine compound that may be present in the composition of the present invention may be N,N-diethyl-3-hydroxybutanamide.

The composition described herein may be useful, with or without further purification or removal of the additional components listed above, in a variety of end use applications. For example, the composition of the present invention can be used as a solvent in an aqueous cleaning composition. Such cleaning compositions, which may further include water and an optional surfactant and/or additive, may effectively remove different types of undesired materials from a variety of substrates, including, for example, those that may present hard surfaces made of metal, glass, plastic, ceramic, porcelain, fiberglass, stone, concrete, plaster, brick, marble, vinyl, natural or composite wood, wall board, or combinations thereof.

Such cleaning compositions may take many forms, including solutions, gels, emulsions, foams, aerosols, pastes, and/or slurries and may be used as or in descaling compositions, a bathroom cleaners, a glass cleaners, a floor cleaners, a biocidal cleaners, an automotive cleaners, a wood cleaners, a plastic cleaners, a paint strippers, a degreasing compositions, a desoiling compositions, and/or an all-purpose general cleaners used on floors, walls, tiles, windows, sinks, showers, bathtubs, shower curtains, wash basins, drains, dishes, fixtures, fittings, counter tops, cabinets, stove tops, appliance surfaces, such as internal and external surfaces of refrigerators, microwave ovens, convection ovens, freezers, dishwashers, washing machines, and dryers.

The preferred forms of the invention described above are to be used as illustration only, and should not be used in a limiting sense to interpret the scope of the present invention. Obvious modifications to the exemplary one embodiment, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

We claim:

1. A composition comprising:
(a) at least one alkyl 3-hydroxybutyrate defined by formula (I):

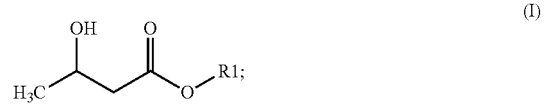

an alkyl butyrate defined by formula (II):

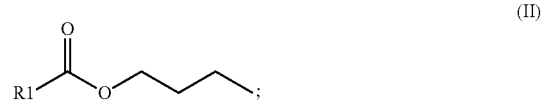

(c) a dimer and/or trimer of said alkyl 3-hydroxybutyrate; and
(d) an alkyl acetate defined by formula (III):

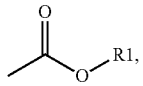
(III)

wherein R1 is an alkyl group selected from the group consisting of isopropyl, n-propyl, isobutyl, n-butyl, 2-butyl (sec-butyl), isopentyl, pentyl, and 2,2-dimethylpropyl, wherein R1 is the same for each of the components defined by formulas (I), (II), and (III),
wherein the total amount of said alkyl butyrate and said alkyl acetate is in the range of from about 50 to about 1500 parts per million by weight (ppmw), based on the total weight of said composition, and
wherein the total amount of said dimer and/or trimer of said alkyl 3-hydroxybutyrate is in the range of from about 50 ppmw to about 1200 ppmw, based on the total weight of said composition.

2. The composition of claim 1, wherein R1 is an alkyl group selected from the group consisting of isobutyl, n-butyl, and 2-butyl.

3. A composition comprising:
(a) at least one alkyl 3-hydroxybutyrate defined by formula (I):

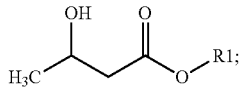
(I)

(b) one or more additional components selected from the group consisting of—
(i) an alkyl butyrate defined by formula (II):

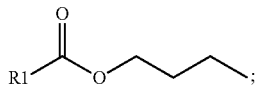
(II)

(ii) a dimer and/or trimer of said alkyl 3-hydroxybutyrate; and
(iii) an alkyl acetate defined by formula (III):

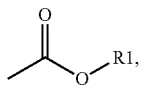
(III)

wherein R1 is an alkyl group selected from the group consisting of isopropyl, n-propyl, isobutyl, n-butyl, 2-butyl (sec-butyl), isopentyl, pentyl, and 2,2-dimethylpropyl, wherein R1 is the same for each of the components defined by formulas (I), (II), and (III), and
further comprising N,N-diethyl-3-hydroxybutanamide in an amount in the range of from about 200 ppmw to about 2000 ppmw, based on the total weight of said composition.

4. A composition comprising:
(a) at least one alkyl 3-hydroxybutyrate defined by formula (I):

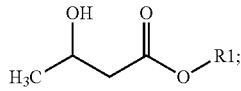
(I)

and
(b) at least one alkyl butyrate defined by formula (II):

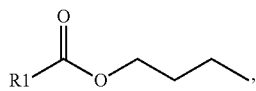
(II)

wherein R1 is an alkyl group having least three and not more than five carbon atoms;
(c) a dimer and/or trimer of said alkyl 3-hydroxybutyrate; and
(d) an alkyl acetate defined by formula (III):

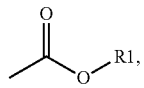
(III)

wherein R1 is the same for each of the components defined by formulas (I), (II), and (III), and
wherein said alkyl 3-hydroxybutyrate is present in said composition in an amount in the range of from about 65 to about 99 weight percent, wherein said alkyl butyrate is present in said composition in an amount in the range of from about 50 ppmw to about 0.1 weight percent, wherein said dimer and/or trimer of said alkyl 3-hydroxybutyrate is present in said composition in an amount in the range of from about 50 to about 1200 ppmw, wherein said alkyl acetate is present in said composition in an amount in the range of from about 50 to about 1000 ppmw, based on the total weight of said composition.

5. The composition of claim 4, wherein said composition comprises not more than about 1 weight percent of components other than said alkyl 3-hydroxybutyrate, said alkyl butyrate, said dimer and/or trimer of said alkyl 3-hydroxybutyrate and said alkyl acetate.

6. The composition of claim 4, wherein R1 is an alkyl group selected from the group consisting of i-butyl, n-butyl, and 2-butyl.

7. A composition comprising:
(a) at least one alkyl 3-hydroxybutyrate defined by formula (I):

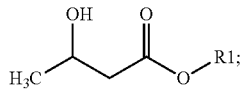
(I)

(b) at least one alkyl butyrate defined by formula (II):

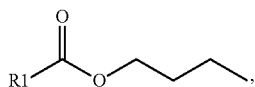
(II)

wherein R1 is an alkyl group having least three and not more than five carbon atoms;
(c) a dimer and/or trimer of said alkyl 3-hydroxybutyrate;
(d) an alkyl acetate defined by formula (III):

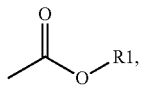
(III)

wherein R1 is the same for each of the components defined by formulas (I), (II), and (III), and
one or more further components selected from the group consisting of—
(e) a first alkyl alcohol defined by formula (IV):

(f) a second alkyl alcohol defined by formula (V):

(g) a second alkyl 3-hydroxybutyrate defined by formula (VI):

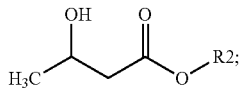
(VI)

and
(h) an alkyl 3-hydroxy-2-methylbutyrate defined by formula (VII):

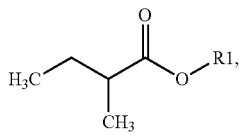
(VII)

wherein R2 is an alkyl group having at least 2 and not more than 4 carbon atoms, wherein R1 in formulas (IV) and (VII) is the same as R1 in formulas (I), (II), and (III) and R2 is the same for each compound in formulas (V) and (VI), wherein said alkyl 3-hydroxybutyrate is present in said composition in an amount in the range of from about 65 to about 99 weight percent, wherein said alkyl butyrate is present in said composition in an amount in the range of from about 50 ppmw to about 0.1 weight percent, wherein said dimer and/or trimer of said alkyl 3-hydroxybutyrate is present in said composition in an amount in the range of from about 50 to about 1200 ppmw, wherein said alkyl acetate is present in said composition in an amount in the range of from about 50 to about 1000 ppmw, wherein the total amount of said first alcohol, said second alcohol, said second alkyl 3-hydroxybutyrate, and said alkyl 3-hydroxy-2-methylbutyrate is not more than about 0.1 weight percent, based on the total weight of said composition.

8. The composition of claim 7, wherein said composition comprises said first alcohol in an amount in the range of from about 3500 to about 10,000 ppmw, wherein said second alcohol is present in said composition in an amount in the range of from about 50 to about 1200 ppmw, wherein said second alkyl 3-hydroxybutyrate is present in said composition in an amount in the range of from about 50 to about 1000 ppmw, wherein said alkyl 3-hydroxy-2-methylbutyrate is present in said composition in an amount in the range of from about 50 to about 1200 ppmw, based on the total weight of said composition.

9. A composition comprising:
(a) at least one alkyl 3-hydroxybutyrate defined by formula (I):

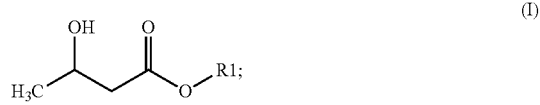
(I)

and
(b) at least one alkyl butyrate defined by formula (II):

(II)

wherein R1 is an alkyl group having least three and not more than five carbon atoms, wherein R1 in formula (I) and R1 in formula (II) are the same and, further comprising N,N-diethyl-3-hydroxybutanamide in an amount in the range of from about 200 ppmw to about 2000 ppmw, based on the total weight of said composition.

* * * * *